United States Patent [19]

Zampini

[11] Patent Number: Plant 7,750

[45] Date of Patent: Dec. 17, 1991

[54] OLIVE PLANT TIZAM

[76] Inventor: James W. Zampini, P.O. Box 122, Perry, Ohio 44081

[21] Appl. No.: 396,470

[22] Filed: Aug. 10, 1989

[51] Int. Cl.[5] ..... A01H 5/00

[52] U.S. Cl. ..... Plt./33

[58] Field of Search ..... Plt./33, 54

[56] References Cited

U.S. PATENT DOCUMENTS

P.P. 1,521 9/1956 Main ..... Plt. 33

P.P. 5,829 12/1986 Haas ..... Plt. 33

*Primary Examiner*—Howard J. Locker

*Attorney, Agent, or Firm*—Watts, Hoffmann, Fisher & Heinke Co.

[57] ABSTRACT

The present invention relates to a new and distinct variety of olive plant, which was discovered by me as a seedling variant growing on my cultivated property at Perry, Ohio. More particularly, the present invention relates to a novel cultivar of *Elaeagnues umbellata* having unusually upright growth and a width at maturity of 5 feet.

5 Drawing Sheets

TECHNICAL FIELD

The present invention relates to a new and distinct variety of olive plant, which was discovered by me in 1976 as a seedling variant growing on my cultivated property at Perry, Ohio. More particularly, the present invention relates to a novel cultivar of *Elaeagnus umbellata* having unusual and distinctive characteristics, which is identified by the varietal reference Tizam.

BACKGROUND OF THE PLANT

The *Elaeagnus umbellata* plant is of the family elaeagneae. The seed parent of my novel cultivar is believed to be *Elaeagnus umbellata* and the pollen parent is unknown. The seed parent is 12 to 18 feet high and 12 to 18 feet, sometimes 20 to 30 feet wide. The leaves are alternate, simple and entire. The leaf shape is elliptic to oblong-ovate and varies from 1 to 4 inches in length. The leaf is bright green on the upperside surface and silver green on the underside surface. The flowers are funnel-shaped, yellowish white, fragrant and ½ inch long. The flowers are borne clustered in groups in the leaf axil. The flowers occur in May to June. The globose fruit is silvery mixed with brown scales turning red while ripening in September to October. The fruit is ¼ to ⅓ inch in diameter. This plant generally has a habit which is spreading.

DESCRIPTION OF THE PREFERRED PLANT VARIETY

Figure 1:
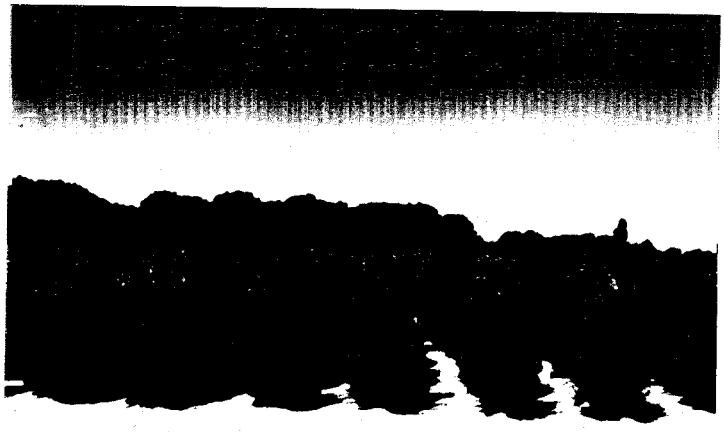
FIG. 1 shows my new Elaeagnus plant in full summer foliage.
Figure 2:
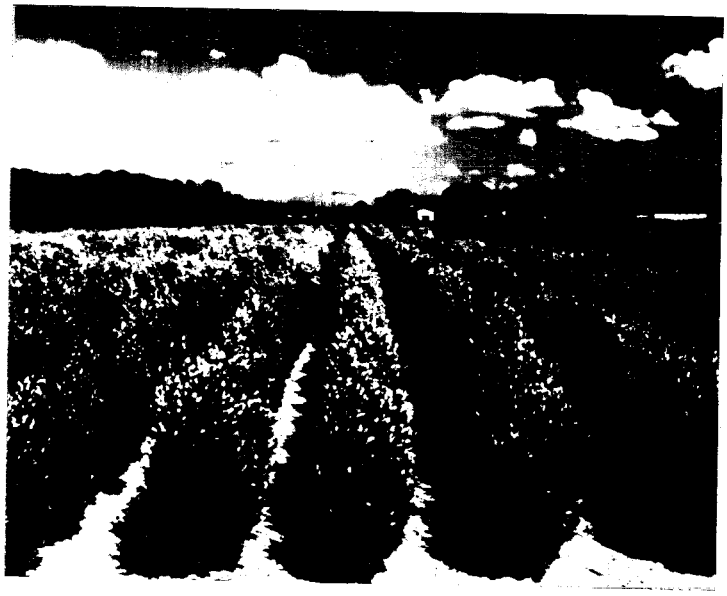
FIG. 2 illustrates the plant in summer displaying the silvery underside surface typical of the species.
Figure 3:
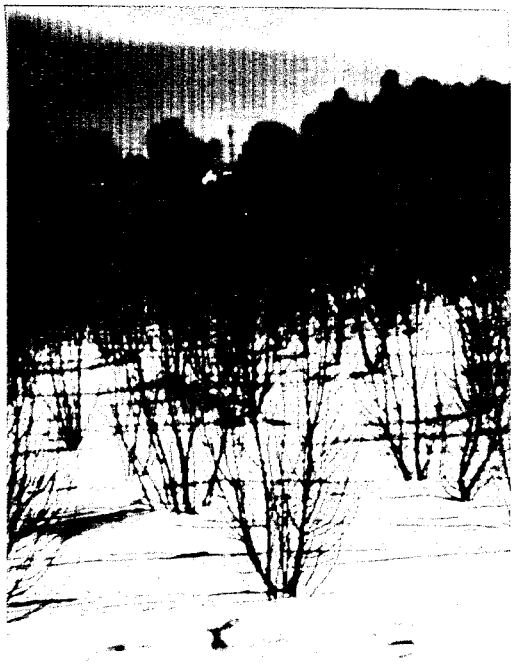
FIG. 3 shows the dormant plant illustrating the unique strong upright branching structure.
Figure 4:
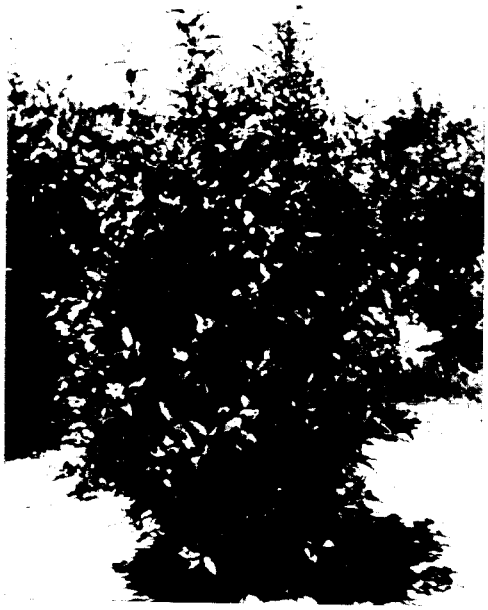
FIG. 4 illustrates the three year old plant in mid season.
Figure 5:
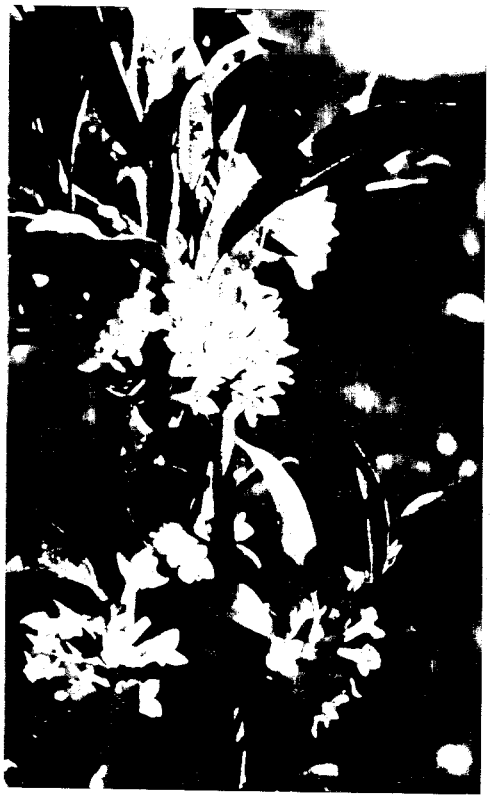
FIG. 5 illustrates a closer view of several blossoms in various stages of opening and some immature leaves.
Figure 6:
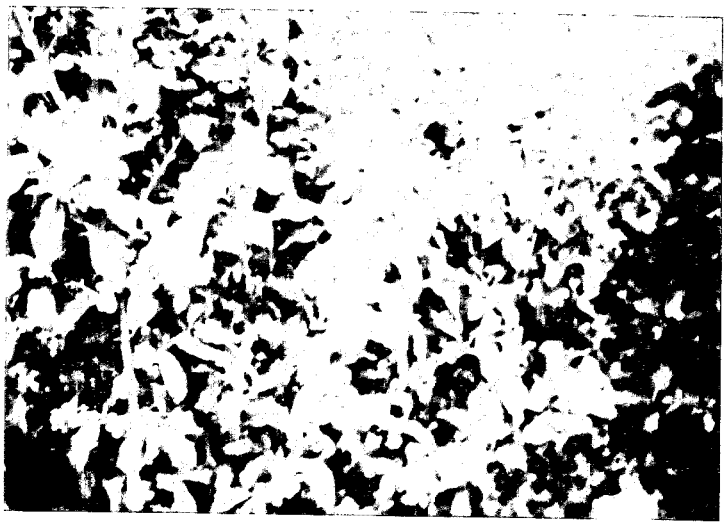
FIG. 6 illustrates the plant with the red fruit.
Figure 7:
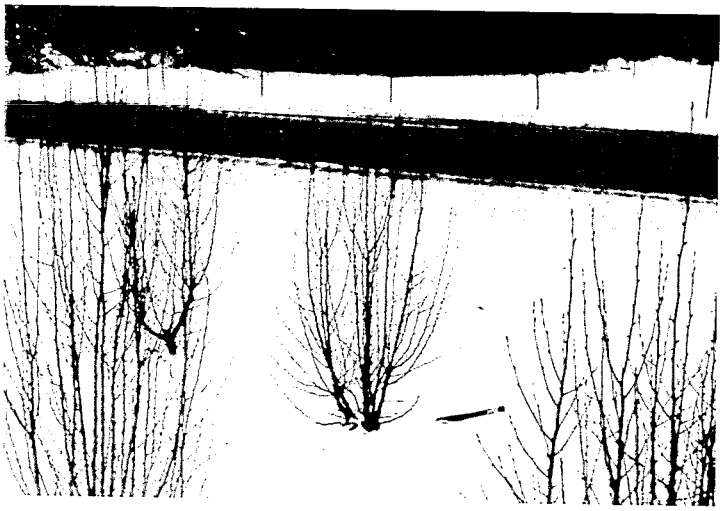
FIG. 7 shows the three year old plant in dormant season illustrating the strong compact upright branching habit.
Figure 8:
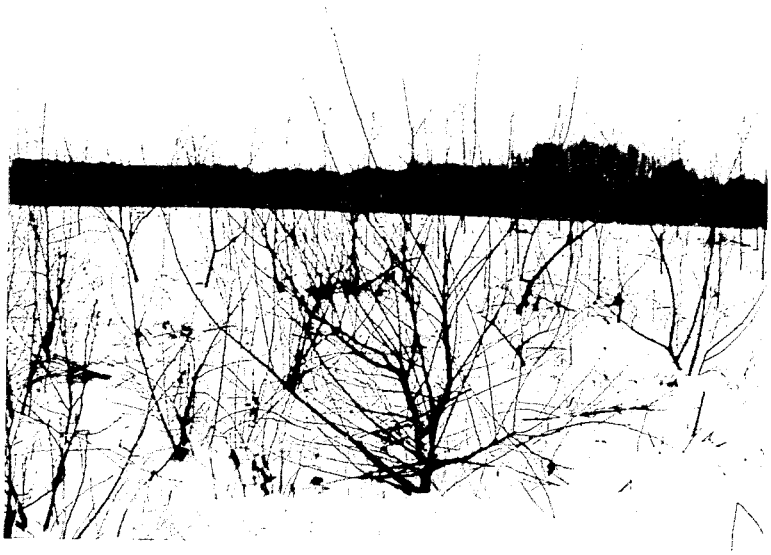
FIG. 8 shows a three year old plant of the seed parent illustrating the spreading branch growth habit.

In this invention, my new Elaeagnus plant is an olive plant with a strong compact upright growth habit. As contrasted with the *Elaeagnus umbellata* species in general, my new plant is about one half the species size under similar growing conditions. As contrasted with the *Elaeagnus umbellata*, my new plant exhibits a more strong upright habit as seen in FIGS. 1, 2, 3, 4, and 7. My new plant is more upright than spreading, which gives it a compact oval appearance.

Asexual reproduction of my new olive plant was performed at Perry, Ohio, Zone 5, by taking softwood cuttings for summer propagation, of which approximately 98% rooted and grew. The cuttings exhibited the same form and growth habit, and had the same strong upright branching habit as described above. Subsequent propagations exhibited the same growth habit. Such reproduction shows the foregoing characteristics and distinctions take place and are established and transmitted through succeeding propagations of the olive plant.

The following is a specific description by way of a specific example of such a new olive cultivar, color terminology being referenced to The Royal Horticultural Society Colour Chart, London, England, 1966, hereinafter referred to as R.H.S. Colour Chart.

Leaves: The leaves are alternate, simple and entire. The leaves have a shape that is elliptic to oblong-ovate, with crisped margin. The length of the leaf blade varies from 1 to 4 inches and the width varies form ¾ to 1½ inches. The leaf tip is obtuse to short-acuminate, and the leaf base is rounded to broadly cuneate. The young leaf normally has silver scales on the uppermost surface, although it is sometimes glabrous, and matures to a medium green. The hue and intensity of the color vary depending on the soil the plant is grown in. The leaf's underside is silver in color, interspersed with brown scales. The leaf is green (R.H.S. Colour Chart Green Group 139B) on the upperside surface and green (R.H.S. Colour Chart Greyed Green Group 188A-D) on the upperside surface in mid season. The petiole length averages around ⅓ inch.

Shrub: The plant at maturity may have a height of approximately 12 feet with the spread being approximately 5 feet giving the overall appearance of the plant being more upright that spreading. Immature twigs are yellowish brown with a silver sheen, darkening in winter to cinnamon brown at the tips. The densely packed scales create a speckled appearance. The leaf buds are covered with cinnamon brown scales in contrast to the yellowish silver branchlet. Second-year wood is silvery brown with brown scales, and frequent spines.

Flower: The flowers occur in May to June in the leaf axil when the young leaves are about ⅓ grown. The flowers are clustered in groups of 1 to 3 or more, and are fragrant. Each flower is ½ inch long, tubular or funnel-shaped with the tube much longer than the limb. The 4 short-stalked stamens are attached to the top of the tube, which is yellowish white in color inside (R.H.S. Colour Chart White Group 155A), and covered with silver scales on the outside. The style is scaly and the 4 lobes are expanded.

Fruit: The fruit is a single-seeded drupe which is globose or sub-globose to ovoid in shape. The fruit color is silver mixed with brown scales, finally turning red (R.H.S. Colour Chart Red Group 44A) when ripe in September to October. The fruit is prolific, nearly encircling the stem, on ¼ to ½ inch long stalks. The fruit is each ¼ to ⅓ inch in diameter.

The characteristics of my new plant which distinguishes it from *Elaeagnus umbellata* is strong upright branching to form a compact oval, as best shown in FIGS. 1, 2, 3, 4 and 7.

A further important and distinguishing characteristic of the present plant variety is that it has a width of approximately 5 feet at maturity.

I claim:

1. A new and distinct cultivar of *Elaeagnus umbellata*, substantially as herein shown and described, characterized particularly by a uniquely upright branching structure and a width at maturity of approximately 5 feet.

* * * * *